US011026570B2

(12) United States Patent
Machida et al.

(10) Patent No.: US 11,026,570 B2
(45) Date of Patent: Jun. 8, 2021

(54) INFORMATION PROCESSING APPARATUS (71) Applicant: CANON KABUSHIKI KAISHA, Tokyo (JP)

(72) Inventors: Kazutoshi Machida, Kawaguchi (JP); Yukio Sakagawa, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 68 days.

(21) Appl. No.: 16/124,724

(22) Filed: Sep. 7, 2018

(65) Prior Publication Data
US 2019/0000311 A1 Jan. 3, 2019

Related U.S. Application Data (63) Continuation of application No. PCT/JP2017/009374, filed on Mar. 9, 2017.

(30) Foreign Application Priority Data

Mar. 11, 2016 (JP) ................. 2016-048703

(51) Int. Cl.
A61B 3/10 (2006.01)
A61B 3/00 (2006.01)
A61B 3/12 (2006.01)
A61B 90/00 (2016.01)

(52) U.S. Cl.
CPC .......... A61B 3/0025 (2013.01); A61B 3/0058 (2013.01); A61B 3/10 (2013.01); A61B 3/102 (2013.01); A61B 3/1233 (2013.01); A61B 2090/364 (2016.02); A61B 2090/3735 (2016.02); A61B 2576/00 (2013.01)

(58) Field of Classification Search
CPC .. A61B 3/102; A61B 3/12; A61B 3/14; A61B 3/10; A61B 5/0066; A61B 3/13
USPC .......................... 351/206, 246; 345/592, 634
See application file for complete search history.

(56) References Cited

U.S. PATENT DOCUMENTS

2012/0050308 A1* 3/2012 Nakano ............... A61B 3/0025
345/592

FOREIGN PATENT DOCUMENTS

| CN | 102056533 A | 5/2011 |
| CN | 104127168 A | 11/2014 |
| CN | 105011900 A | 11/2015 |
| DE | 102013210728 A1 | 12/2014 |
| JP | 2014-45869 A | 3/2014 |
| JP | 2014-217423 A | 11/2014 |
| JP | 2015-083276 A | 4/2015 |

* cited by examiner

Primary Examiner — Hung X Dang
(74) Attorney, Agent, or Firm — Canon U.S.A., Inc. IP Division (57) ABSTRACT An information processing apparatus includes a first acquisition portion acquiring a front image of an eye fundus, a second acquisition portion acquiring an En-Face image on the basis of a plurality of tomographic images of the eye fundus, and a display control portion controlling a display unit to display the En-Face image in a superimposed relation to the front image. The display control portion changes a depth range, at the eye fundus, of the En-Face image superimposed on the front image.

20 Claims, 9 Drawing Sheets

FIG. 6C

INFORMATION PROCESSING APPARATUS

CROSS-REFERENCE TO RELATED APPLICATIONS

This application is a Continuation of International Patent Application No. PCT/JP2017/009374, filed Mar. 9, 2017, which claims the benefit of Japanese Patent Application No. 2016-048703, filed Mar. 11, 2016, both of which are hereby incorporated by reference herein in their entirety.

TECHNICAL FIELD

The technique disclosed herein relates to an information processing apparatus for processing an image of an examination target eye.

BACKGROUND ART

An OCT (Optical Coherence Tomography) apparatus is used to obtain a tomographic image of the fundus of an examination target eye.

Patent Literature (PTL) 1 discloses a technique of producing an En-Face image, which is a two-dimensional image in the case of viewing the eye fundus from the front in a pseudo-manner, by using pixels in a predetermined layer among a plurality of tomographic images obtained by the OCT apparatus. PTL 1 further states that the En-Face image and an SLO (Scanning Laser Ophthalmoscope) image obtained by an SLO are displayed side by side.

CITATION LIST

Patent Literature

PTL 1 Japanese Patent Laid-Open No. 2014-45869

However, PTL 1 has a problem that, because the SLO image and the En-Face image are displayed side by side, an examiner is required to move a sight line over a distance for comparison between the SLO image and the En-Face image.

One object of the disclosed technique is to reduce a distance through which a sight line is to be moved when observing both the SLO image and the En-Face image.

The disclosed technique is not limited to the above object, and the intention of aiming at advantageous effects, which are obtained with various features described later in EXAMPLES and which are not obtained with any related art, can also be regarded as another object of the disclosed technique.

SUMMARY OF INVENTION

To achieve the above object, an information processing apparatus disclosed herein includes a first acquisition portion acquiring a front image of an eye fundus, a second acquisition portion acquiring an En-Face image on the basis of a plurality of tomographic images of the eye fundus, and a display control portion controlling a display unit to display the En-Face image in a superimposed relation to the front image, wherein the display control portion changes a depth range, at the eye fundus, of the En-Face image superimposed on the front image.

Further features of the present invention will become apparent from the following description of exemplary embodiments with reference to the attached drawings.

DESCRIPTION OF EMBODIMENTS

An ophthalmic apparatus and an information processing apparatus, disclosed herein, will be described below with reference to FIGS. 1A to and 6D. It is to be noted that configurations described in the following EXAMPLES are merely illustrative, and that the present invention is not limited by the following EXAMPLES.

Example 1

Basic Configuration of Apparatus

A basic configuration of the ophthalmic apparatus according to EXAMPLE 1 will be described below with reference to FIGS. 1A, 1B and 1C.

Figure 1A:
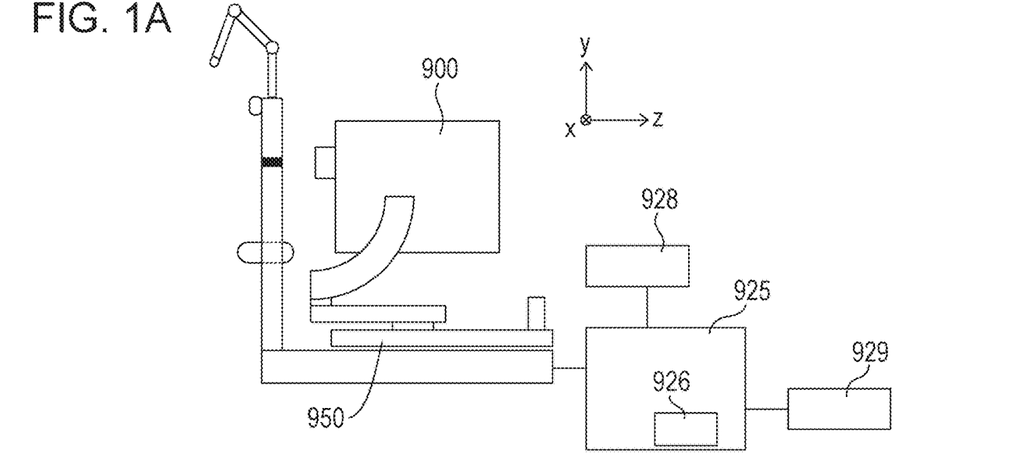
FIG. 1A illustrates one example of a basic configuration of an ophthalmic apparatus.
Figure 1B:
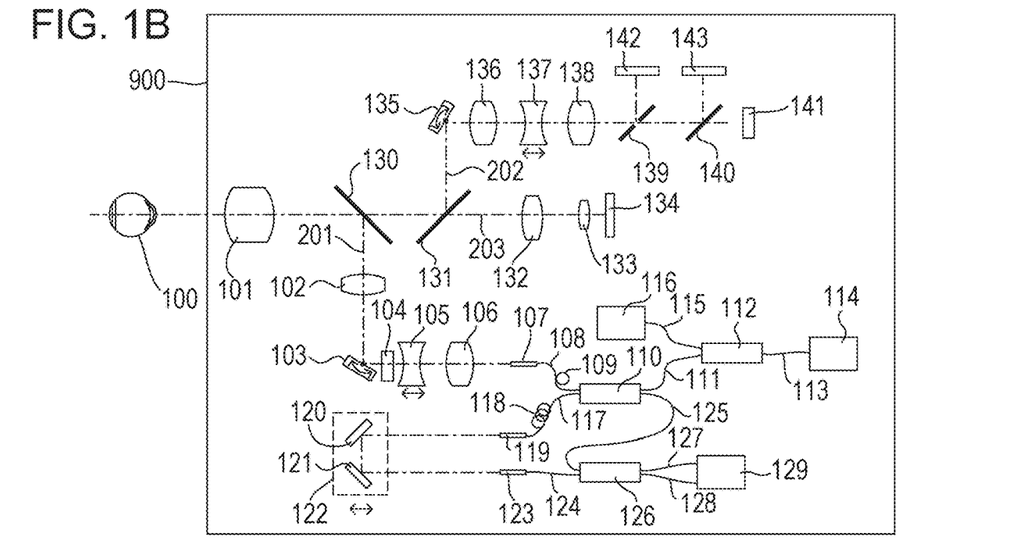
FIG. 1B illustrates one example of a configuration of an optical system in OCT.

FIG. 1A illustrates a configuration of the ophthalmic apparatus. Numeral 900 denotes an optical head including a measurement optical system to capture a two-dimensional image (SLO image) and a tomographic image of an eye fundus. Numeral 950 denotes a stage unit capable of moving the optical head in the xyz-directions in the drawing.

Numeral 925 denotes a personal computer (information processing apparatus) that controls the stage unit, and that produces a front image, a tomographic image, and an En-Face image. When OCTA is selected as an image capturing method, the information processing apparatus 925 further produces an OCTA En-Face image, for example.

Numeral 926 denotes a storage unit that stores various kinds of information. Numeral 928 denotes a display unit. The display unit 928 is, for example, a liquid crystal monitor. Numeral 929 denotes an input unit through which an instruction is input to the personal computer. More specifically, the input unit 929 is constituted by a keyboard and a mouse. Alternatively, the input unit 929 may be a touch panel.

Configurations of optical systems included in the optical head 900, i.e., configurations of a measurement optical system, a reference optical system, and sections around light sources in the illustrated EXAMPLE, will be described below with reference to FIG. 1B.

The measurement optical system is first described. An objective lens 101 is disposed to face an examination target eye 100. An optical path is branched for each of wavelength bands, by a first dichroic mirror 130 and a second dichroic mirror 131 both disposed on an optical axis of the objective lens 101, into an optical path 201 for an OCT optical system, an optical path 202 for an SLO optical system and a fixation lamp, and an optical path 203 for observation of an anterior eye.

Light reflected by the eye fundus propagates along the optical path 202 via an XY scanner 135, and is received by an avalanche photodiode (APD) 142 via an aperture mirror 139. Although the XY scanner 135 is illustrated as one mirror, it is constituted by an X scanner and a Y scanner to be able to perform scanning in two-axis directions. Lights from an SLO light source 143 for observation of the eye fundus and from a fixation lamp 141 enter the optical path 202 via a third dichroic mirror 140. Numerals 136, 137 and 138 denote lenses. The lens 137 is driven by a motor (not illustrated) for focusing of the light from the fixation lamp and the light for observation of the eye fundus. The SLO light source 143 emits light with a center wavelength of 780 nm. The fixation lamp 141 generates visible light and prompts a patient to look at a fixation point.

In the optical path 203, numerals 132 and 133 denote lenses, and numeral 134 denotes an infrared CCD for observation of the anterior eye. The CCD 134 has sensitivity for a wavelength of not-illustrated illumination light for observation of the anterior eye, more specifically a wavelength of about 970 nm.

The optical path 201 constitutes the OCT optical system as described above, and is used to capture the tomographic image of the fundus of the examination target eye 100. More specifically, the optical path 201 is used to obtain an interference signal for forming the tomographic image. Numeral 102 denotes a lens, 104 denotes a shutter for allowing the examination target eye to be illuminated with light only during an image capturing operation, and 103 denotes an XY scanner for scanning the light over the eye fundus. Although the XY scanner 103 is illustrated as one mirror, it is constituted to be able to perform scanning in XY two-axis directions. Numerals 105 and 106 denote lenses. The lens 105 is driven by a not-illustrated motor to make focusing of light from a light source 114, the light being output from a fiber 108 connected to a fiber coupler 110, onto the fundus of the examination target eye 100. With such focusing, light from the fundus of the examination target eye 100 is also focused as a spot image at a fore end of the fiber 108 and enters the fiber 108 at the same time.

Configurations of an optical path extending from the light source 114 toward the examination target eye and the reference optical system will be described below.

The light source 114 is a wavelength swept light source capable of changing a wavelength, and it emits light with a center wavelength of 1040 nm and a band width of 100 nm, for example. The above-mentions values are merely illustrative, and the center wavelength and the band width are not limited to those values. The light emitted from the light source 114 is introduced to a fiber coupler 112 through a fiber 113, and is branched to a fiber 115 for measurement of light intensity and a fiber 111 for OCT measurement. Power of the light emitted from the light source 114 is measured by a PM (Power Meter) 116 after passing through the fiber 115. The light having passed through the fiber 111 is introduced to a fiber coupler 110. The fiber coupler 110 functions as a divider for dividing an optical path through which the light from the light source 114 is transferred, into a reference optical path and a measurement optical path. In other words, the light from the light source 114 is branched to measurement light (also called OCT measurement light) and reference light by the fiber coupler 110. A branch ratio of the fiber coupler 112 is 99:1, and a branch ratio of the fiber coupler 110 is 90 (reference light):10 (measurement light). The above-mentioned values are merely illustrative, and the branch ratios are not limited to those values.

The measurement light branched by the fiber coupler 110 is output as parallel light from a collimator 107 after passing through the fiber 108. Numeral 109 denotes a polarization adjuster on the measurement light side, which is disposed midway the optical fiber 108. Such a polarization adjuster includes several portions in which the optical fiber is routed in the form of loops, and it is able to adjust polarization states of the measurement light and the reference light to be matched with each other by rotating the loop-like portions about the lengthwise direction of the fiber, and by applying torsion to the fiber. In the apparatus of this EXAMPLE, it is assumed that the polarization states of the measurement light and the reference light are adjusted and fixed in advance.

The measurement light output from the collimator 107 passes through the measurement optical system, and is able to scan a region spanning over the desired range at the fundus of the examination target eye 100.

On the other hand, the reference light branched by the fiber coupler 110 is output as parallel light from a collimator 119 after passing through a fiber 117 and a polarization adjuster 118. The output reference light is reflected by reference mirrors 120 and 121 on a coherence gate stage 122, and then reaches a fiber coupler 126 through a collimator 123 and a fiber 124.

The coherence gate stage 122 functions as an alteration unit for changing positions of the reference mirrors 120 and 121 in the direction of the optical axis, and adjusts the optical path length of the reference light with that function. The mirrors 120 and 121 are adjusted such that a position at which the optical path length of the measurement light and the optical path length of the reference light are equal to each other is located near an image capturing target. The coherence gate stage 122 is driven by a not-illustrated motor to be adapted for the difference in axial length of the examination target eye, and so on.

The fiber coupler 126 functions as a multiplexer for multiplexing the reference light having passed through the reference optical path and the measurement light having passed through the measurement optical path. Thus, the measurement light and the reference light having reached the fiber coupler 126 are multiplexed to become interference light. After passing through fibers 127 and 128, the interference signal is converted to an electrical signal by a balanced receiver 129 that is an optical detector for detecting the multiplexed light. The information processing apparatus 925 receives an output from the balanced receiver 129. Then, the information processing apparatus 925 executes general reconstruction processing on the received signal, and produces a tomographic image.

The foregoing is a process of acquiring information regarding a cross-section at one point of the examination target eye 100. The ophthalmic apparatus can provide a two-dimensional tomographic image by performing the above-mentioned process plural times in the X direction. Furthermore, the ophthalmic apparatus can provide a three-dimensional tomographic image by performing the above-mentioned process plural times in each of the X direction and the Y direction. Scanning to obtain the two-dimensional or three-dimensional tomographic image is performed by the X scanner and/or the Y scanner.

The X scanner and the Y scanner are constituted by deflection mirrors arranged such that rotation axes of the deflection mirrors are orthogonal to each other. The X scanner performs the scanning in the X-axis direction, and the Y scanner performs the scanning in the Y-axis direction. The X-axis direction and the Y-axis direction are directions perpendicular to the axial direction of the examination target eye 100, and are perpendicular to each other.

Although the configuration of SS-OCT has been described in the above example, SD-OCT may also be used.

Explanation of OCTA

OCTA in this EXAMPLE will be described below with reference to FIG. 1C.

In OCTA, from the viewpoint of measuring time-dependent changes of the interference signal due to a blood stream, it is desired to obtain a plurality of tomographic images at the same place of the eye fundus. In this EXAMPLE, the OCT apparatus performs scanning of repeating a B scan m times at the same place of the eye fundus for each of a number n of Y positions.

Figure 1C:
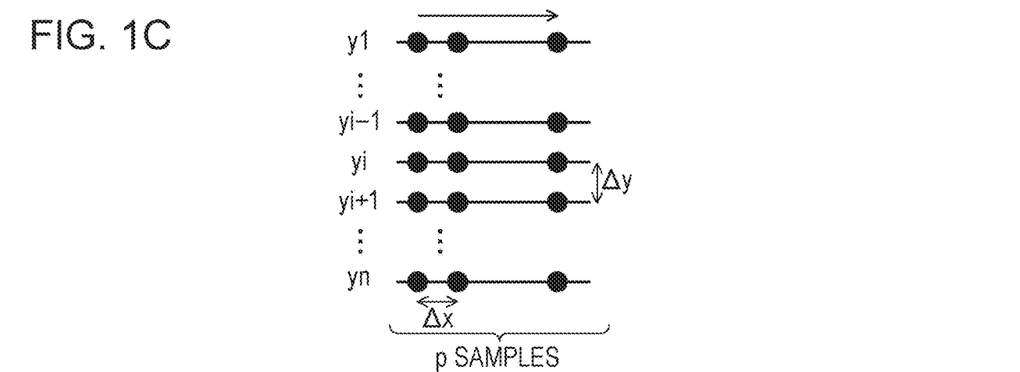
FIG. 1C illustrates one example of a scanning method in OCT.

FIG. 1C illustrates a practical example of a scanning method. The OCT apparatus performs the B scan m times at each of the number n of Y positions y1 to yn on a flat plane of the eye fundus. When m has a larger value, the number of times of measurements at the same place is increased, and detection accuracy of the blood stream is improved. On the other hand, a scan time is prolonged, thus causing problems that a motion artifact generates in an image due to an eye motion (fine motion in the fixation) during the scanning, and that the burden on the patient increases. In this EXAMPLE, m=3 is set in consideration of balance between the above-described two points. The number of repetition times of the B scan is not limited to 3. The value of m may be optionally changed depending on the speed of an A scan in the OCT apparatus and the amount of the motion of the examination target eye 100. Moreover, p denotes the number of samplings of the A scan per B scan. Thus, a planar image size is determined by p×n. When p×n has a larger value, a wider region can be scanned on condition of a measurement pitch being the same, but the scan time is prolonged, thus causing the above-described problems with the motion artifact and the burden on the patient. In FIG. 1C, $\Delta x$ denotes an interval between adjacent X positions (i.e., an x pitch), and $\Delta y$ denotes an interval between adjacent Y positions (i.e., a y pitch). In this EXAMPLE, the x pitch is set to ½ of a beam spot size of the illumination light at the eye fundus, i.e., 10 μm. Furthermore, $\Delta y$ is also set to 10 μm as with $\Delta x$. The above-mentioned values are merely illustrative, and they may be changed as appropriate. Although $\Delta y$ may be set to a value greater than 10 μm for the purpose of shorting the scan time, $\Delta y$ is preferably increased within such a range as not exceeding 20 μm, i.e., the beam spot size. Regarding the x pitch and the y pitch, when the beam spot size at the eye fundus is increased, precision degrades, but an image over a wider range can be obtained with a smaller data capacity. The x pitch and the y pitch may be optionally changed depending on clinical demands.

The information processing apparatus 925 acquires, as a motion contrast value, correlation or variance per pixel in images among the three B scans obtained at each Y position. Then, the information processing apparatus 925 can acquire a three-dimensional OCTA image by assigning a luminance value to each motion contrast value. For instance, the information processing apparatus 925 may assign a higher luminance value to a larger variance, or may assign a higher luminance value to a smaller correlation value.

Explanation of Image Processing Method

An image processing method in this EXAMPLE will be described below with reference to FIG. 2.

Figure 2:
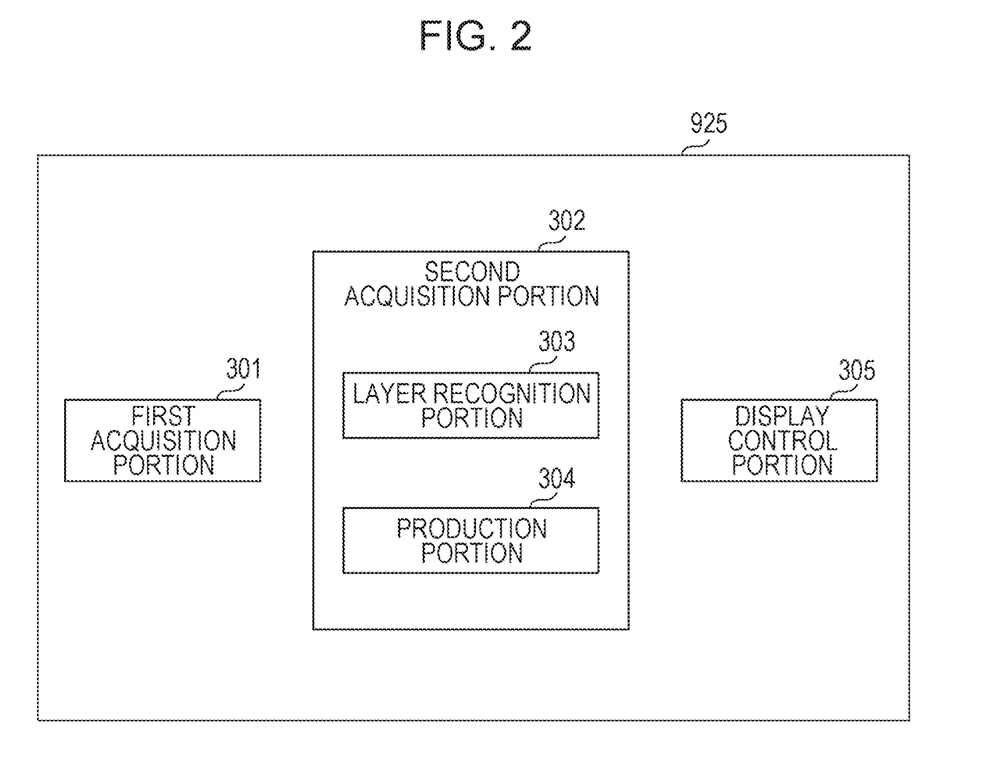
FIG. 2 illustrates one example of functions of an information processing apparatus.

FIG. 2 illustrates a functional configuration of the information processing apparatus 925. The information processing apparatus 925 functions as a first acquisition portion 301, a second acquisition portion 302, a layer recognition portion 303, a production portion 304, and a display control portion 305 with a not-illustrated processor, such as a CPU, executing programs stored in a storage unit 926.

The number of CPUs incorporated in the information processing apparatus 925 may be one or plural. The storage unit 926 may include a plurality of memories. In other words, when at least one processor (such as a CPU) and at least one memory are connected and the at least one processor executes programs stored in the at least one memory, the processor in the information processing apparatus 925 functions as the above-described individual portions.

The first acquisition portion 301 acquires the tomographic image on the basis of an output from the balanced receiver 129. Furthermore, the first acquisition portion 301 acquires the front image (also called the SLO image hereinafter) of the eye fundus on the basis of an output from the APD 142. Moreover, the first acquisition portion 301 acquires the three-dimensional OCTA image. More specifically, the first acquisition portion 301 calculates the correlation among the number m of tomographic images produced on the basis of the interference signals that are obtained with the B scans repeated m times. The first acquisition portion 301 acquires the three-dimensional OCTA image on the basis of the correlation among the tomographic images by executing the above-described calculation of the correlation for each of the plural Y positions. For instance, the first acquisition portion 301 acquires the OCTA image in which blood streams are emphasized, by assigning higher luminance to the position where the correlation is lower. The OCTA image can be produced using various known methods, and hence detailed description of a manner of producing the OCTA image is omitted.

The second acquisition portion 302 acquires two types of En-Face images. More specifically, the second acquisition portion 302 acquires not only an OCTA En-Face image, but also an intensity En-Face image. Here, the intensity En-Face image stands for an En-Face image obtained from a plurality of ordinary tomographic images each representing the signal intensity, and it is different from the OCTA En-Face image that is obtained from the three-dimensional OCTA image. The second acquisition portion 302 includes the layer recognition portion 303 and the production portion 304.

The layer recognition portion 303 extracts a layer structure of a measurement target (retina) in the tomographic image obtained in the first acquisition portion 301, and recognizes a shape of each layer boundary. The layer boundary can be recognized by known methods, such as a method of recognizing the layer boundary on the basis of luminance change in the depth direction.

The layer recognition portion 303 recognizes layer boundaries between various layers, such as RNFL, GCL, INL, ONL+IS, OS, RPE, and BM. Shapes of the specified layer boundaries are input to the production portion 304 together with the tomographic image.

The production portion 304 produces the intensity En-Face image by, on the basis of the layer boundary recognized by the layer recognition portion 303, integrating (or averaging) pixel values of a pixel value sequence in a predetermined depth range of the tomographic image for each pixel value sequence (i.e., per A scan). Alternatively, the production portion 304 may produce the intensity En-Face image by selecting one pixel value from the pixel value sequence in the predetermined depth range of the tomographic image for each pixel value sequence. Furthermore, the production portion 304 produces the OCTA En-Face image by, on the basis of the layer boundary recognized by the layer recognition portion 303, integrating (or averaging) pixel values of the pixel value sequence in the predetermined depth range for each pixel value sequence (i.e., per A scan) from the three-dimensional OCTA image. Alternatively, the production portion 304 may produce the OCTA En-Face image by selecting one pixel value from the pixel value sequence in the predetermined depth range of the three-dimensional OCTA image for each pixel value sequence. Since the three-dimensional OCTA image and the tomographic image from which the layer boundary has been obtained are the common tomographic image, the production portion 304 can easily specify, on the three-dimensional OCTA image, a position of the layer boundary that has been obtained by the layer recognition portion 303. Various known methods can be used to produce the En-Face image without being limited to the above-described example. For instance, although the depth range (i.e., the depth range at the eye fundus) in the tomographic image used to produce the En-Face image is described above as being determined on the basis of the layer boundary, it may be determined from a plurality of horizontal linear lines perpendicular to the depth direction.

Figure 3A:
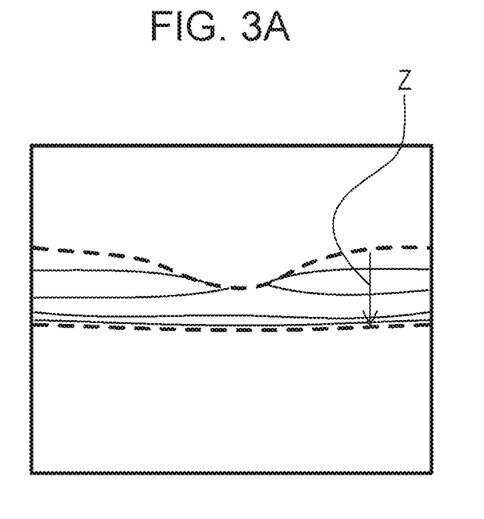
FIGS. 3A and 3B illustrate one example of a method for setting a depth range in a tomographic image.
Figure 3B:
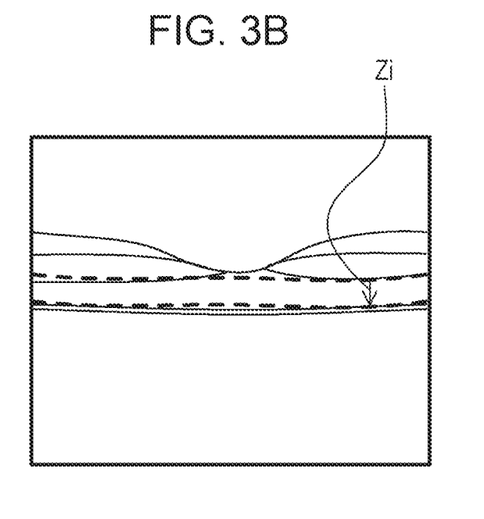

When the depth range for which the En-Face image is to be produced is changed in accordance with an instruction from the input unit 929, the production portion 304 produces the En-Face image again each time the instruction is issued. Accordingly, the En-Face image in the depth range corresponding to an operator's demand is produced as appropriate by the production portion 304. For instance, the change of the depth range using the input unit can be implemented by moving the layer boundary superimposed on the tomographic image with dragging, by way of example, as illustrated in FIGS. 3A and 3B. The production portion 304 may produce the En-Face image when the production portion 304 detects that the layer boundary has been dragged and dropped. Alternatively, when the production portion 304 detects that the layer boundary has been dragged, the production portion 304 may produce the En-Face image regardless of whether the layer boundary has been dropped or not. The layer boundary may be moved with rotation of a mouse wheel without being limited to the dragging.

As an alternative, the production portion 304 may be constituted to produce the En-Face image by using information of the layer boundary, which information is obtained from an external storage device (not illustrated), and the tomographic image.

The display control portion 305 makes control to selectively display, on the display unit 928, the tomographic image and the front image both acquired by the first acquisition portion 301, and the luminance and the OCTA En-Face image both acquired by the second acquisition portion 302. For instance, the display control portion 305 makes control to display, on the display unit 928, the luminance and the OCTA En-Face image in a superimposed relation to the front image. When the depth range for which the En-Face image is to be produced is changed in accordance with an instruction from the input unit 929, the display control portion 305 sequentially displays, on the display unit, the En-Face image again each time the En-Face image is produced by the production portion 304.

One example of operation of the ophthalmic apparatus having the above-described configuration will be described below with reference to FIGS. 4, 5 and 6A to 6D.

Figure 4:
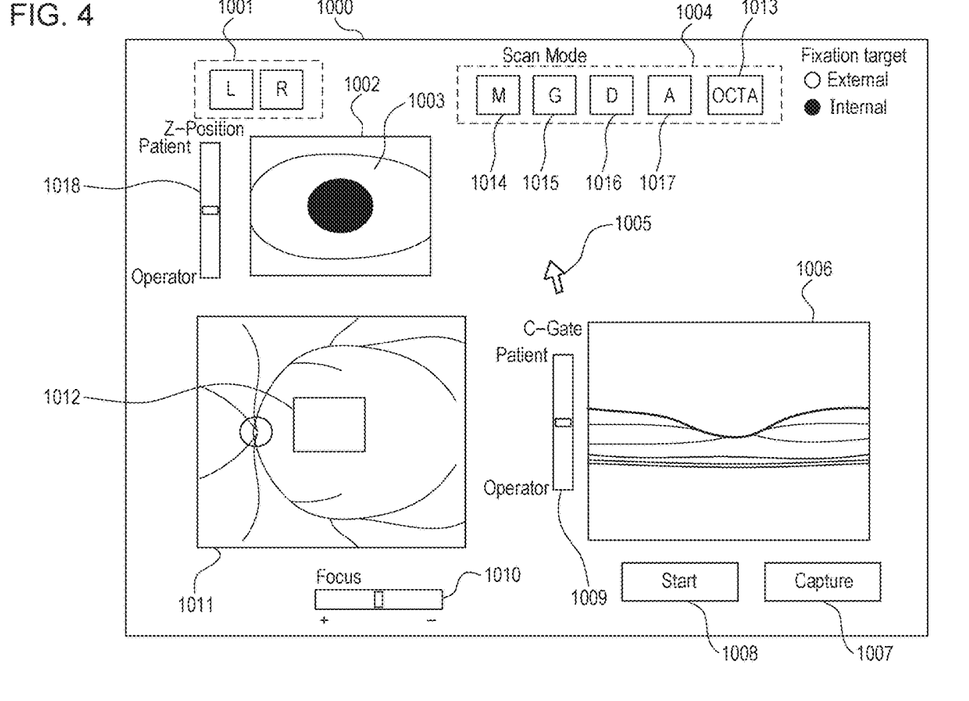
FIG. 4 illustrates one example of a captured-image display screen.
Figure 5:
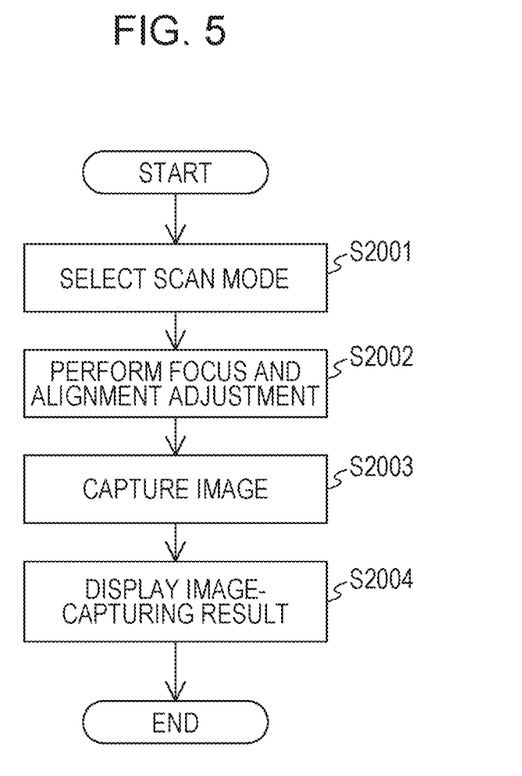
FIG. 5 illustrates one example of an image capturing flow.

FIG. 5 is a flowchart illustrating one example of image capturing procedures. It is premised that the display control portion 305 displays a display screen, illustrated in FIG. 4, on the display unit 928. Numeral 1001 gives an indication denoting which one of the left eye and the right eye is displayed. Furthermore, in FIG. 4, an anterior eye image 1003 is displayed in an area 1002, and an eye fundus image 1012 is displayed in an area 1011 in a superimposed relation to an image capturing region of the tomographic image. Moreover, the tomographic image is displayed in an area 1006. A mouse cursor 1005 movable with operation of the input unit 929 is also displayed.

In step S2001, a scan mode is selected by the operator. Stated in another way, the processor incorporated in the information processing apparatus 925 recognizes a scan mode selected by the operator. More specifically, the operator selects, with the aid of the input unit 929, a desired scan mode from Scan Mode buttons 1004 on a measurement screen 1000 illustrated in FIG. 4. The Scan Mode buttons 1004 include a Macula 3D button 1014, a Glaucoma 3D button 1015, a Disc 3D button 1016, an Anterior 3D button 1017, and an OCTA button 1013. When any scan mode button is clicked, the processor incorporated in the information processing apparatus 925 recognizes the clicked scan mode, and sets a scan pattern and a fixation position optimum for the scan mode in the OCT apparatus. Examples of the scan pattern include a 3D scan, a radial scan, a cross scan, a circle scan, and a raster scan.

Next, in step S2002, upon detecting depression of a Start button 1008, the processor incorporated in the information processing apparatus 925 controls the OCT apparatus to automatically perform focus adjustment and alignment adjustment. When performing fine adjustment of the focus and the alignment, the operator moves and adjusts a position of the optical head in the Z direction relative to the examination target eye using a slider 1018, performs the focus adjustment using a slider 1010, and performs position adjustment of the coherence gate using a slider 1019.

In step S2003, upon detecting depression of a Capture button 1007, the processor incorporated in the information processing apparatus 925 controls the OCT apparatus to capture an image of the examination target eye in accordance with the scan pattern having been set. When the image capturing is performed by the OCT apparatus, images (such as the SLO image, the OCT image, the En-Face image, and the three-dimensional OCTA image) of the examination target eye are acquired by the first acquisition portion 301 and the second acquisition portion 302.

In step S2004, the display control portion 305 displays the images of the examination target eye on the display unit 928.

FIGS. 6A, 6B, 6C and 6D illustrate examples of an image-capturing result screen displayed on the display unit 928 by the display control portion 305 in step S2004. In an image-capturing result screen 3100 illustrated in FIG. 6A, an intensity En-Face image 3104 is displayed in a first display area 3102 in a superimposed relation to a front image (SLO image) 3103 of the eye fundus. The size and the position of the intensity En-Face image 3104 can be changed with operation (e.g., drag and drop) of the input unit 929. More specifically, the display control portion 305 receives a signal from the input unit 929 and controls the display unit 928 to change the size and the position of the region of the intensity En-Face image 3104. In an initial state, the OCTA En-Face image may be displayed in the first display area 3102 instead of the intensity En-Face image.

Figure 6A:
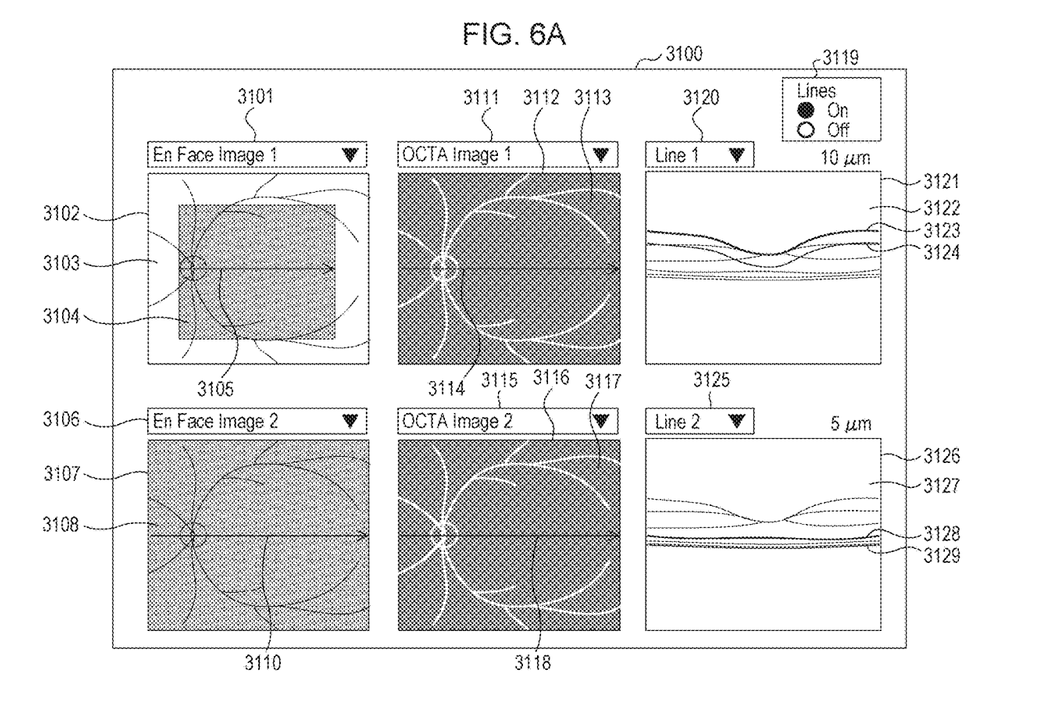
FIGS. 6A, 6B, 6C and 6D illustrate examples of an image-capturing result screen.

An image to be superimposed on the front image 3103 can be selected by choosing any of the intensity En-Face image, the OCTA En-Face image, the SLO image, and a projection image from a pull-down menu 3101. For instance, upon detecting that the OCTA En-Face image is selected from the pull-down menu 3101, the display control portion 305 displays the OCTA En-Face image on the display unit 928 instead of the intensity En-Face image. The projection image is an image produced by taking the average over an entire range in the depth direction, and is different from the En-Face image produced using a partial range in the depth direction.

An OCTA En-Face image 3113 in the same depth range as the intensity En-Face image 3104 is displayed in a second display area 3112. Any of the intensity En-Face image, the OCTA En-Face image, the SLO image, and the projection image can be selected from a pull-down menu 3111. For instance, upon detecting that the intensity En-Face image is selected from the pull-down menu 3111, the display control portion 305 displays the intensity En-Face image on the display unit 928 instead of the OCTA En-Face image.

In a third display area 3121, there is displayed a tomographic image 3122 corresponding to the position of a line 3105 in the SLO image 3103, the line 3105 indicating the position at which the tomographic image is obtained, is displayed. The line 3105 can be moved by dragging it with the aid of the input unit 929. The display control portion 305 detects the position of the line 3105 and displays, on the display unit 928, the tomographic image corresponding to the detected position. A line 3114 displayed in a superimposed relation to the OCTA En-Face image 3113 has the same function as the line 3105, and hence detailed description of the line 3114 is omitted. The display control portion 305 controls the display unit 928 in such a manner that, when one of the line 3105 and the line 3114 is moved, the other line is also moved in conjunction with the one line.

The layer boundary recognized by the layer recognition portion 303 is also displayed as a boundary line 3123 in a superimposed relation to the tomographic image 3122. Furthermore, a boundary line 3124 is also displayed in a superimposed relation to the tomographic image 3122 at a position that is spaced through a predetermined distance (e.g., 10 μm) from the boundary line 3123 in the depth direction. The above-mentioned two boundary lines may be specified in terms of depth range by designating specific layer boundaries, such as RPE and ILM. The depth range specified by the boundary line 3123 and the boundary line 3124 represents the depth range of the intensity En-Face image 3104 and the OCTA En-Face image 3113.

Upon detecting that a desired boundary (RNFL, GCL, INL, ONL+IS, OS, RPE or BM) between the retina layers is selected from a pull-down menu 3120, the display control portion 305 controls the display unit 928 to change the display positions of the boundary line 3123 and the boundary line 3124 depending on the selected layer boundary. The positions of the boundary line 3123 and the boundary line 3124 can be optionally changed by dragging those lines with the aid of the input unit 929 independently of each other. As an alternative, the boundary line 3123 and the boundary line 3124 may be moved while maintaining a certain spacing therebetween instead of being independently of each other.

An intensity En-Face image 3108 in a depth range different from that of the intensity En-Face image 3104 is displayed in a fourth display area 3107. An OCTA En-Face image 3117 in the same depth range as that of the intensity En-Face image 3108 is displayed in a fifth display area 3116. A tomographic image 3127 corresponding to the position of a line 3110 in the intensity En-Face image 3108, the line 3110 indicating a position at which the tomographic image is obtained, is displayed in a sixth display area 3126. Positions of a boundary line 3128 and a boundary line 3129 are different from the positions of the boundary line 3123 and the boundary line 3124 such that states of the eye fundus at different positions in the depth direction can be checked individually. Functions of lines 3110 and 3118 are the same as those of the lines 3105 and 3114, and hence detailed description of the lines 3110 and 3118 is omitted. The lines 3105, 3110, 3114 and 3118 may be made in conjunction with one another such that the positions of all those lines represent the same position of the eye fundus. In addition, pull-down menus 3106, 3115 and 3125 have the same functions as those of the pull-down menus 3101, 3111 and 3120, and hence description of the pull-down menus 3106, 3115 and 3125 is omitted.

In order to increase viewability of the OCTA En-Face image, the lines 3105, 3110, 3114 and 3118 may be set to be not displayed in the initial state in which the screen of FIG. 6A is displayed. In such a case, whether or not to display the lines 3105, 3110, 3114 and 3118 can be switched over using a display switch button 3119. Thus, the display control portion 305 detects an operation made on the display switch button 3119, and executes control on whether the lines 3105, 3110, 3114 and 3118 are to be displayed or not. In a mode other than the OCTA mode, an image-capturing result screen similar to that illustrated in FIG. 6A is displayed although the OCTA En-Face image is not included. Thus, in the area in which the OCTA En-Face image is displayed in FIG. 6A, the OCTA En-Face image is replaced with the intensity En-Face image or the projection image, for example. In such a case, the display control portion 305 may control the display unit 928 to display the line indicating the position of the tomographic image in the initial state of the image-capturing result screen. In other words, whether or not to display the line indicating the position of the tomographic image in the initial state of the image-capturing result screen may be switched over depending on the image capturing mode.

While, in the above EXAMPLE, the SLO image is displayed in the first display area 3102, another image, such as the En-Face image or the OCTA image, may be displayed there. Moreover, in the initial state, the OCTA En-Face image instead of the intensity En-Face image 3104 may be displayed in the first display area in a superimposed relation to the SLO image.

According to the above EXAMPLE, since the intensity En-Face image or the OCTA En-Face image is displayed in a superimposed relation to the SLO image that is one example of the front image, the movement of a sight line when comparing the En-Face image and the front image can be reduced.

Furthermore, since the intensity En-Face image or the OCTA En-Face image, which is superimposed on the SLO image 3103, and the OCTA En-Face image 3112 are changed in conjunction with each other when the depth position is changed, the operator can easily change the plurality of En-Face images.

Example 2

Figure 6B:
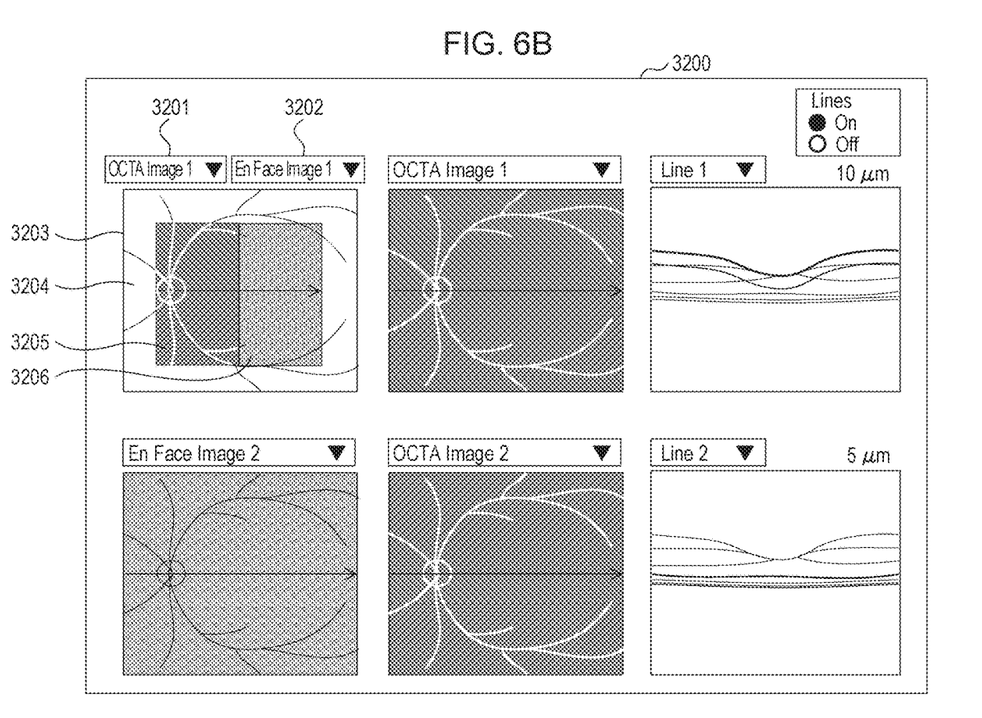

EXAMPLE 2 will be described below with reference to FIG. 6B. A configuration of an ophthalmic apparatus is the same as that in EXAMPLE 1, and hence description of the configuration of the ophthalmic apparatus is omitted. EXAMPLE 2 is different from EXAMPLE 1 in the image-capturing result screen. In FIG. 6B, second to sixth display areas are similar to those of the image-capturing result screen according to EXAMPLE 1 illustrated in FIG. 6A, and hence description of the second to sixth display areas is omitted.

In a first display area 3203 in FIG. 6B, an OCTA En-Face image 3205 and an intensity En-Face image 3206 are displayed in a superimposed relation to a front image (SLO image) 3204 of the eye fundus. The OCTA En-Face image 3205 is displayed on the left side and the intensity En-Face image 3206 is displayed on the right side in FIG. 6B, but the displayed positions of both the images may be reversed in the left-right direction.

Although the OCTA En-Face image 3205 is displayed in the first display area 3203, an image to be displayed can be changed by selecting any of the intensity En-Face image, the SLO image, and the projection image from a pull-down menu 3201. Similarly, although the intensity En-Face image 3206 is displayed in the first display area 3203, an image to be displayed can be changed by selecting any of the OCTA En-Face image, the SLO image, and the projection image from a pull-down menu 3202. More specifically, the display control portion 305 receives the type of an image selected by each of the pull-down menus 3201 and 3202, and controls the display unit 928 to display the selected image in a superimposed relation to the SLO image 3204. As in EXAMPLE 1, when the depth range of the En-Face image is changed by changing the positions of the boundary lines 3123 and 3124, the OCTA En-Face image 3205 and the intensity En-Face image 3206 are updated by the display control portion 305.

According to the above-described EXAMPLE, since the intensity En-Face image and the OCTA En-Face image are displayed in a superimposed relation to halves of the SLO image, an advantageous effect of enabling different types of En-Face images to be checked without operation of switching over the different types of En-Face images is obtained in addition to the advantageous effects of EXAMPLE 1.

While areas of the intensity En-Face image and the OCTA En-Face image are set to the same size, the sizes of those areas may be designed to be changeable, for example, by dragging boundaries of both the En-Face images. In other words, when the display control portion 305 detects movements of the boundaries of both the En-Face images, the display control portion 305 controls the display unit 928 to change the sizes of the areas of the En-Face image and the OCTA En-Face image.

The areas of the intensity En-Face image and the OCTA En-Face image may be given as areas divided in the up-down direction instead of the left-right direction.

When the positions of the boundary lines 3123 and 3124 are changed, only the En-Face image on the SLO image 3204, that En-Face image being the same type as the En-Face image displayed in the second display area, may be updated.

Example 3

Figure 6C:
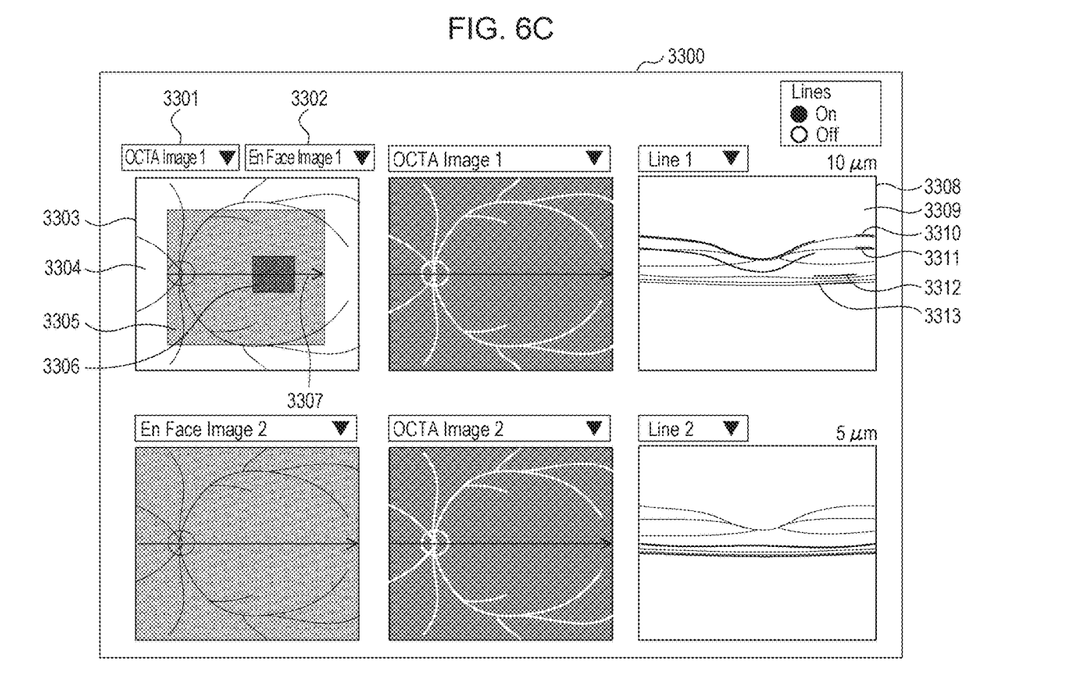

EXAMPLE 3 will be described below with reference to FIG. 6C. A configuration of an ophthalmic apparatus is the same as that in EXAMPLE 1, and hence description of the configuration of the ophthalmic apparatus is omitted. EXAMPLE 3 is different from EXAMPLE 1 in the image-capturing result screen. In FIG. 6C, second and fourth to sixth display areas are similar to those of the image-capturing result screen according to EXAMPLE 1 illustrated in FIG. 6A, and hence description of the second and fourth to sixth display areas is omitted.

In a first display area 3303A, there is displayed a front image (SLO image) 3304 of the eye fundus on which an intensity En-Face image 3305 is superimposed. An OCTA En-Face image 3306 is further displayed on the intensity En-Face image 3305. The displayed intensity En-Face image 3305 can be changed by selecting any of the OCTA En-Face image, the SLO image, and the projection image from a pull-down menu 3301.

Similarly, the displayed OCTA En-Face image 3306 can also be changed by selecting any of the intensity En-Face image, the SLO image, and the projection image from a pull-down menu 3302. More specifically, the display control portion 305 controls the display unit 928 to display the selected image with the aid of the pull-down menus 3301 and 3302.

A tomographic image 3309 corresponding to a line 3307 in the SLO image 3304 is displayed in a third display area 3308. The intensity En-Face image 3305 is an En-Face image in a depth direction range that is sandwiched between a boundary line 3310 and a boundary line 3311. The OCTA En-Face image 3306 is an En-Face image in a depth direction range that is sandwiched between a boundary line 3312 and a boundary line 3313. The display control portion 305 controls the display unit 928 to display the individual boundary lines and En-Face images in a manner of clearly indicating that the intensity En-Face image 3305 corresponds to the boundary lines 3310 and 3311, and that the OCTA En-Face image 3306 corresponds to the boundary lines 3312 and 3313. For instance, the display control portion 305 controls the display unit 928 to display an outer frame of each En-Face image in the same color as that of the corresponding boundary line.

The operator can operate the boundary lines 3310 and 3311 and the boundary lines 3312 and 3313 independently of each other. Accordingly, the depth ranges of both the En-Face images can be individually set in this EXAMPLE.

The OCTA En-Face image displayed in the second area corresponds to the depth direction range that is specified by the positions of the boundary lines 3312 and 3313. The OCTA En-Face image displayed in the second area may be updated only when the boundary lines 3312 and 3313 indicating the depth direction range of the OCTA En-Face image is changed. In other words, when the boundary lines 3310 and 3311 are changed in FIG. 6C, only the intensity En-Face image 3305 may be updated by the display control portion 305.

Furthermore, in response to a signal from the input unit 929, the display control portion 305 may control the display unit 928 to change the size and the position of the OCTA En-Face image 3306. For instance, when the position of the OCTA En-Face image 3306 is changed, the display control portion 305 controls the display unit 928 to change positions in the horizontal direction at which the boundary lines 3312 and 3313 are displayed in the third display area.

While, in EXAMPLE illustrated in FIG. 6C, the OCTA En-Face image 3306 is displayed on part of the intensity En-Face image 3305, the intensity En-Face image may be displayed on part of the OCTA En-Face image.

According to this EXAMPLE, the different types of En-Face images can be individually set in the depth direction.

Example 4

Figure 6D:
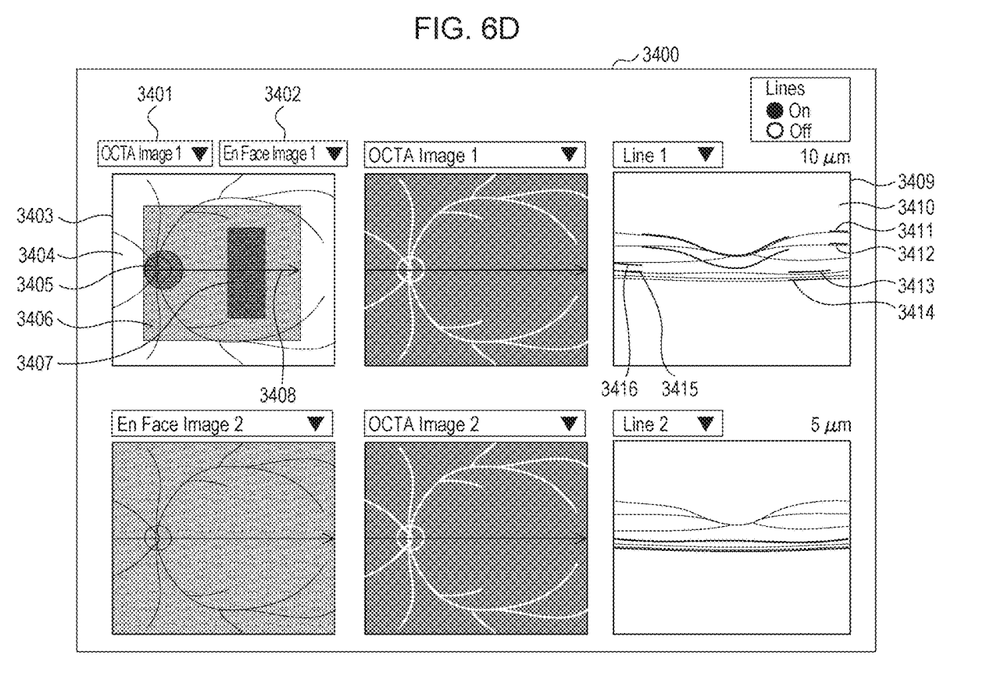

EXAMPLE 4 will be described below with reference to FIG. 6D. A configuration of an ophthalmic apparatus is the same as that in EXAMPLE 1, and hence description of the configuration of the ophthalmic apparatus is omitted. EXAMPLE 4 is different from EXAMPLE 1 in the image-capturing result screen. In FIG. 6D, second and fourth to sixth display areas are similar to those of the image-capturing result screen according to EXAMPLE 1 illustrated in FIG. 6A, and hence description of the second and fourth to sixth display areas is omitted.

In a first display area 3403, there is displayed a front image (SLO image) 3404 of the eye fundus on which an intensity En-Face image 3406 is superimposed. OCTA En-Face images 3405 and 3407 are further displayed in a superimposed relation to the intensity En-Face image 3406.

By setting a region of the OCTA En-Face image 3405 to have a circular shape with the display control portion 305, the operator can observe an image near the optic disk in the depth direction. The size and the shape of the region of the OCTA En-Face image 3405 can be optionally changed in accordance with an instruction input from the input unit 929. More specifically, the display control portion 305 controls the display unit 928 to change the shape of the region of the En-Face image in accordance with an input from the input unit 929.

The displayed intensity En-Face image 3406 can be changed by selecting any of the OCTA En-Face image, the SLO image, and the projection image from a pull-down menu 3401. Similarly, the displayed OCTA En-Face images 3405 and 3407 can also be each changed by selecting any of the intensity En-Face image, the SLO image, and the projection image from a pull-down menu 3402.

A tomographic image 3410 corresponding to a line 3408 in the SLO image 3404 is displayed in a third display area 3409. The intensity En-Face image 3406 is an En-Face image in a depth direction range that is sandwiched between a boundary line 3411 and a boundary line 3412. The OCTA En-Face image 3405 is an En-Face image in a depth direction range that is sandwiched between boundary lines 3415 and 3416. Similarly, the OCTA En-Face image 3407 is an En-Face image in a depth direction range that is sandwiched between boundary lines 3413 and 3414.

As in EXAMPLE 3, the display control portion 305 controls the display unit 928 to display the individual boundary lines and En-Face images in a manner of clearly indicating correspondence relations between the En-Face images and the boundary lines. More specifically, as in EXAMPLE 3, the correspondence relations between the En-Face images and the boundary lines may be indicated using colors.

In FIG. 6D, even for the same type of En-Face image, two En-Face images in different ranges in the depth direction, i.e., the OCTA En-Face images 3405 and 3407, can be set individually. More specifically, even when the boundary lines 3413 and 3414 are changed with the aid of the input unit 929, the display control portion 305 controls the display unit 929 to update only the OCTA En-Face image 3407 without updating the OCTA En-Face image 3405. Accordingly, the operator can observe different images of the same type of En-Face image in different depth ranges at a glance. In other words, the display control portion 305 can control the display unit 928 to display the OCTA En-Face image different in depth range at the eye fundus in each of regions of the front image.

The depth direction range of the OCTA En-Face image displayed in the second display area may be made in conjunction with any one of the OCTA En-Face images 3405 and 3407. In another example, the OCTA En-Face image displayed in the second display area may be made in conjunction with one of the OCTA En-Face images 3405 and 3407, the one having a larger region or the one having a smaller region.

While, in EXAMPLE illustrated in FIG. 6D, the plurality of OCTA En-Face images 3405 and 3407 are displayed on part of the intensity En-Face image 3406, a plurality of intensity En-Face images may be displayed on part of the OCTA En-Face image. Alternatively, the OCTA En-Face images 3405 and 3407 may be directly superimposed on the SLO image 3304 without displaying the intensity En-Face image 3406.

According to this EXAMPLE, the operator can recognize plural images of the same type of En-Face image in different ranges in the depth direction at a glance. It is also possible to change a shape of each En-Face image. Hence the En-Face images suitable for the intended purpose can be displayed.

Other Examples

In EXAMPLES described above, the displayed image is changed using the pull-down menu. However, when the display unit 928 includes a touch panel, the displayed image may be changed with tapping on an image.

While, in EXAMPLES described above, the En-Face image is superimposed on the SLO image, the SLO image may be superimposed on the En-Face image.

While, in EXAMPLES described above, the SLO image is displayed, by way of example, as the front image of the eye fundus, an eye fundus image captured by an eye fundus camera may be handled as the front image.

While EXAMPLES have been described in detail above, the disclosed technique can be implemented as a system, an apparatus, a method, a program, or a recording medium (storage medium), for example. More specifically, the disclosed technique may be applied to a system constituted by a plurality of devices (such as a host computer, an interface device, an image capturing device, and a web application), or may be applied to an apparatus constituted by a single device.

Furthermore, the present invention can be implemented with a process of supplying a program, which realizes one or more functions of EXAMPLES described above, to a system or an apparatus via a network or a storage medium, and reading and executing the program by one or more processors in a computer of the system or the apparatus. Moreover, the present invention can be implemented with a circuit (e.g., ASIC) that realizes the one or more functions.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An information processing apparatus comprising:
a first acquisition portion acquiring a front image of an eye fundus;
a second acquisition portion acquiring an En-Face image on basis of a plurality of tomographic images of the eye fundus; and
a display control portion controlling a display unit to display the En-Face image in a superimposed relation to the front image and two boundary lines in a superimposed relation to the tomographic image,
wherein a depth range of the En-Face image is defined by the two boundary lines, and
wherein the display control portion changes a depth range, at the eye fundus, of the En-Face image superimposed on the front image by moving each of the two boundary lines on the tomographic image.

2. The information processing apparatus according to claim 1, wherein the En-Face image is an OCTA En-Face image.

3. The information processing apparatus according to claim 2, wherein the display control portion controls the display unit to display the OCTA En-Face image different in depth range at the eye fundus in each of regions of the front image.

4. The information processing apparatus according to claim 1, wherein the display control portion controls the display unit to display another En-Face image different in size from the En-Face image superimposed on the front image, and the display control portion changes the depth range, at the eye fundus, of the En-Face image superimposed on the front image in conjunction with a depth range, at the eye fundus, of the other En-Face image different in size from the En-Face image superimposed on the front image.

5. The information processing apparatus according to claim 4, wherein the display control portion controls the display unit to display the other En-Face image not in a superimposed relation to the front image in a larger size than the En-Face image superimposed on the front image.

6. The information processing apparatus according to claim 5, wherein the display control portion controls the display unit to display the front image and the other En-Face image having a larger size than the En-Face image superimposed on the front image side by side.

7. The information processing apparatus according to claim 1, wherein the second acquisition portion acquires an intensity En-Face image and an OCTA En-Face image, and the display control portion controls the display unit to display the intensity En-Face image and the OCTA En-Face image in a superimposed relation to the front image at same time.

8. The information processing apparatus according to claim 7, wherein the display control portion controls the display unit to display the intensity En-Face image and the OCTA En-Face image, both the En-Face images being different in depth range at the eye fundus from each other.

9. The information processing apparatus according to claim 7, wherein the display control portion controls the display unit to display the OCTA En-Face image in a superimposed relation to the intensity En-Face image.

10. The information processing apparatus according to claim 1, wherein the display control portion controls the display unit to change a size and a shape of the En-Face image and a position of the En-Face image in the front image.

11. The information processing apparatus according to claim 1, wherein the movement of the boundary line is carried out according to the instructions of the operator.

12. An information processing method comprising the steps of:
acquiring a front image of an eye fundus and an En-Face image on basis of a plurality of tomographic images of the eye fundus; and
controlling a display unit to display the En-Face image in a superimposed relation to the front image and two boundary lines in a superimposed relation to the tomographic image,
wherein a depth range of the En-Face image is defined by the two boundary lines, and
wherein the display control portion changes the depth range, at the eye fundus, of the En-Face image superimposed on the front image by moving each of the two boundary lines on the tomographic image.

13. An information processing apparatus comprising:
a first acquisition portion acquiring a front image of an eye fundus;
a second acquisition portion acquiring an En-Face image on basis of a plurality of tomographic images of the eye fundus; and
a display control portion controlling a display unit to display the En-Face image, the front image and two boundary lines in a superimposed relation to the tomographic image,
wherein a depth range of the En-Face image is defined by the two boundary lines, and
wherein the display control portion changes a depth range, at the eye fundus, of the En-Face image displayed on the display unit by moving each of the two boundary lines on the tomographic image.

14. The information processing apparatus according to claim 13, wherein the En-Face image is an OCTA En-Face image.

15. The information processing apparatus according to claim 13, wherein the movement of the boundary line is carried out according to instructions of an operator.

16. The information processing apparatus according to claim 13, wherein the display control portion changes a depth position, at the eye fundus, of the En-Face image displayed on the display unit by moving the two boundary lines while maintaining a spacing therebetween.

17. The information processing apparatus according to claim 16, wherein the movement of the two boundary lines is carried out according to instructions of an operator.

18. An information processing apparatus comprising:
an acquisition portion acquiring an En-Face image on basis of a plurality of tomographic images of an eye fundus; and
a display control portion controlling a display unit to display the En-Face image, and two boundary lines in a superimposed relation to the tomographic image,
wherein a depth range and a depth position of the En-Face image are defined by the two boundary lines, and
wherein the display control portion changes (A) the depth range, at the eye fundus, of the En-Face image displayed on the display unit when each of the two boundary lines on the tomographic image is moved by an operator, (B) the depth position, at the eye fundus, of the En-Face image displayed on the display unit when the two boundary lines while maintaining a spacing therebetween are moved by the operator.

19. An information processing method comprising the steps of:
acquiring a front image of an eye fundus and an En-Face image on basis of a plurality of tomographic images of the eye fundus; and
controlling a display unit to display the En-Face image, the front image and two boundary lines in a superimposed relation to the tomographic image,
wherein a depth range of the En-Face image is defined by the two boundary lines, and
whe the display control portion changes the depth range, at the eye fundus, of the En-Face image displayed on the display unit by moving each of the two boundary lines on the tomographic image.

20. An information processing method comprising the steps of:
acquiring an En-Face image on basis of a plurality of tomographic images of an eye fundus; and
controlling a display unit to display the En-Face image and two boundary lines in a superimposed relation to the tomographic image,
wherein a depth range and a depth position of the En-Face image are defined by the two boundary lines, and
wherein the display control portion changes (A) the depth range, at the eye fundus, of the En-Face image displayed on the display unit when each of the two boundary lines on the tomographic image is moved by an operator, (B) the depth position, at the eye fundus, of the En-Face image displayed on the display unit when the two boundary lines while maintaining a spacing therebetween are moved by the operation.

* * * * *